(12) United States Patent
Rynerson

(10) Patent No.: US 11,826,564 B2
(45) Date of Patent: Nov. 28, 2023

(54) METHODS AND DEVICES FOR TREATING SKIN CONDITIONS

(71) Applicant: BlephEx, LLC, Franklin, TN (US)

(72) Inventor: James M. Rynerson, Franklin, TN (US)

(73) Assignee: BLEPHEX, LLC, Brentwood, TN (US)

( * ) Notice: Subject to any disclaimer, the term of this patent is extended or adjusted under 35 U.S.C. 154(b) by 0 days.

(21) Appl. No.: 17/748,945

(22) Filed: May 19, 2022

(65) Prior Publication Data
US 2022/0280785 A1    Sep. 8, 2022

Related U.S. Application Data

(63) Continuation of application No. PCT/US2021/058329, filed on Nov. 5, 2021.

(60) Provisional application No. 63/110,290, filed on Nov. 5, 2020.

(51) Int. Cl.
| | | |
|---|---|---|
| *A61N 1/32* | (2006.01) | |
| *A61N 1/36* | (2006.01) | |
| *A61N 1/20* | (2006.01) | |
| *A61N 1/04* | (2006.01) | |
| *A61N 1/08* | (2006.01) | |

(52) U.S. Cl.
CPC ............. *A61N 1/328* (2013.01); *A61N 1/205* (2013.01); *A61N 1/323* (2013.01); *A61N 1/3601* (2013.01); *A61N 1/36034* (2017.08); *A61N 1/0492* (2013.01); *A61N 2001/083* (2013.01)

(58) Field of Classification Search
CPC ..................................................... A61N 1/328
See application file for complete search history.

(56) References Cited

U.S. PATENT DOCUMENTS

| | | | | |
|---|---|---|---|---|
| 6,119,038 | A * | 9/2000 | Cook | A61N 1/328 604/20 |
| 8,868,204 | B2 * | 10/2014 | Ron Edoute | A61N 1/328 607/66 |
| 2002/0099323 | A1 | 7/2002 | Dev et al. | |
| 2005/0010205 | A1 | 1/2005 | Hovda et al. | |
| 2005/0015119 | A1 | 1/2005 | Beck et al. | |
| 2010/0210994 | A1 | 8/2010 | Zarif | |
| 2011/0282180 | A1 | 11/2011 | Goldkuhl et al. | |
| 2015/0012079 | A1 * | 1/2015 | Goroszeniuk | A61N 1/0484 607/148 |
| 2015/0374984 | A1 * | 12/2015 | King | A61N 1/0468 607/50 |
| 2016/0089309 | A1 * | 3/2016 | Mohammadi | A61K 8/0212 604/20 |

(Continued)

FOREIGN PATENT DOCUMENTS

| | | |
|---|---|---|
| WO | WO-2017181951 A1 | 10/2017 |
| WO | WO-2022099067 A1 | 5/2022 |

OTHER PUBLICATIONS

International Search Report and Written Opinion dated Jan. 31, 2022 for International Application No. PCT/US2021/058329.

(Continued)

*Primary Examiner* — Michael W Kahelin
(74) *Attorney, Agent, or Firm* — Wilson Sonsini Goodrich & Rosati

(57) ABSTRACT

Provided are methods and devices for treating skin conditions using an electrical signal applied to the skin of a subject.

11 Claims, 9 Drawing Sheets

(56) References Cited

U.S. PATENT DOCUMENTS

2016/0296269 A1* 10/2016 Rubinsky .............. A61B 18/12
2019/0247234 A1* 8/2019 Prakash ................. A61N 1/30

OTHER PUBLICATIONS

International Preliminary Report on Patentability dated May 19, 2023 for International Application No. PCT/US2021/058329.

* cited by examiner

METHODS AND DEVICES FOR TREATING SKIN CONDITIONS

CROSS-REFERENCE TO RELATED APPLICATIONS

The present application is a continuation of International Application Serial No. PCT/US2021/058329, filed Nov. 5, 2021, which claims the benefit of U.S. Provisional Patent Application No. 63/110,290, filed on Nov. 5, 2020, the entirety of which is incorporated herein by reference.

BACKGROUND

Chronic conditions of the eye, such as blepharitis and dry eye, have confounded medicine's best efforts at treatment for a very long time. The etiology of many chronic conditions of the eye, such as blepharitis and dry eye, has been thought to comprise several causes and that such a plurality of causes was the reason an effective treatment has eluded practitioners. Bacteria are thought to play a major causative role in various chronic conditions, including blepharitis and dry eye.

Biofilms, which can comprise an extracellular matrix of proteins and polysaccharides, are important for the survival of bacteria in nature, as bacteria do not survive well outside of such microenvironments. It is thought that biofilms may contribute to the establishment and progression of certain chronic diseases, such as gingivitis, ear infections, gastrointestinal ulcers, urinary tract infections, and even some pulmonary infections. However, as the biofilm builds on a surface, it can become highly resistant to traditional treatments of bacteria, such as the use of antibiotics.

Blepharitis, which can comprise inflammation of the eyelid is a serious and very common (e.g., in older patients) condition that may eventually leads to destruction of the tear glands, potentially resulting in dry eye disease. In view of poor results observed in antibiotic treatment of bacteria in biofilms, new methods of treating chronic conditions blepharitis and its causes are needed.

SUMMARY

Provided herein are embodiments of a device for providing an electrical therapy to a skin of a subject comprising: a transmission surface comprising a first electrode and a second electrode; a power supply in electrical communication with the first and second electrodes; a controller to regulate voltage, current, or a combination thereof of an electrical signal supplied the first and second electrodes the first and second electrodes by the power supply.

In some embodiments, the controller supplies a first voltage to the first electrode, and a second voltage to the second electrode, thereby creating a voltage potential between the first electrode and the second electrode. In some embodiments, the first and second electrode contact a skin surface to generate an electric current across through the skin. In some embodiments, said first voltage and second voltage are selected to vaporize a bio-film.

In some embodiments, the device further comprises a feedback loop to measure an impedance of the skin, and wherein the controller regulates the electrical signal based on a measured impedance.

In some embodiments, the voltage of the electrical signal is about 0.1 to 20 volts (V). In some embodiments, the current of the electrical signal is less than about 5 milliamps (mA).

In some embodiments, the device further comprises an enclosure to house the power supply and the controller, wherein a wire lead extends from the enclosure to the transmission surface. In some embodiments, the current of the electrical signal is an alternating current. In some embodiments, the current of the electrical signal is a direct current.

In some embodiments, the electrical therapy is used to treat acne, snoring, dry eye, premature aging, or a combination thereof.

Provided herein are embodiments of a method of applying an electrical therapy on a skin of a subject, the method comprising: contacting a skin surface with a first electrode and a second electrode; generating an electrical current through the skin by supplying a first voltage to the first electrode and a second voltage to the second electrode, wherein the first voltage is different than the second voltage.

In some embodiments, the electrical current is less than about 5 milliamps. In some embodiments, the first voltage and the second voltage are about 0.1 to 20 volts (V). In some embodiments, the method further comprises applying a solution to the skin surface to reduce electrical resistivity of the skin.

In some embodiments, the electrical therapy is an acne reduction therapy. In some embodiments, the acne reduction therapy reduces instances of Acne Rosacea inflammation.

In some embodiments, the generation of the electrical current vaporizes a biofilm. In some embodiments, the electrical therapy treats a snoring condition. In some embodiments, the skin surface is proximal to a nasal cavity. In some embodiments, the first and second electrodes are provided on a transmission surface, and wherein said transmission surface comprises a curvature adapted to conform to a bridge of a nose. In some embodiments, the first and second electrodes are provided on a transmission surface.

In some embodiments, the electrical therapy treats a premature aging condition. In some embodiments, the electrical therapy treats a dry eye condition.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
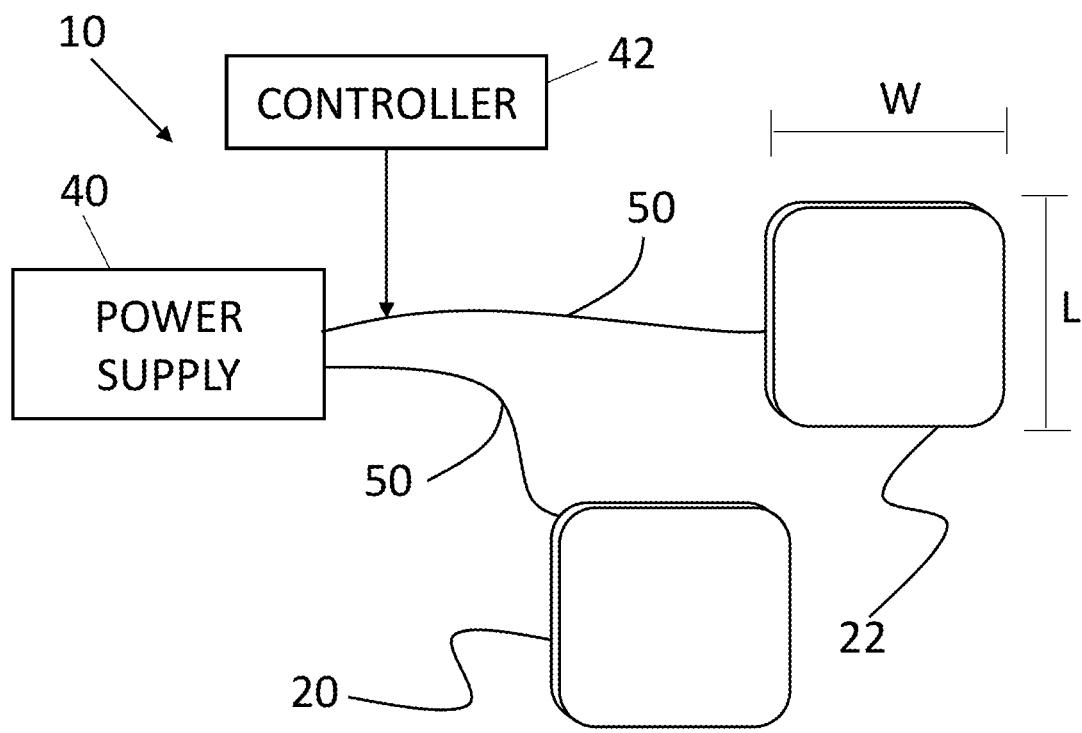
FIG. 1A depicts a schematic of a system for applying electric energy to a target area of a subject, according to some embodiments herein.
Figure 1B:
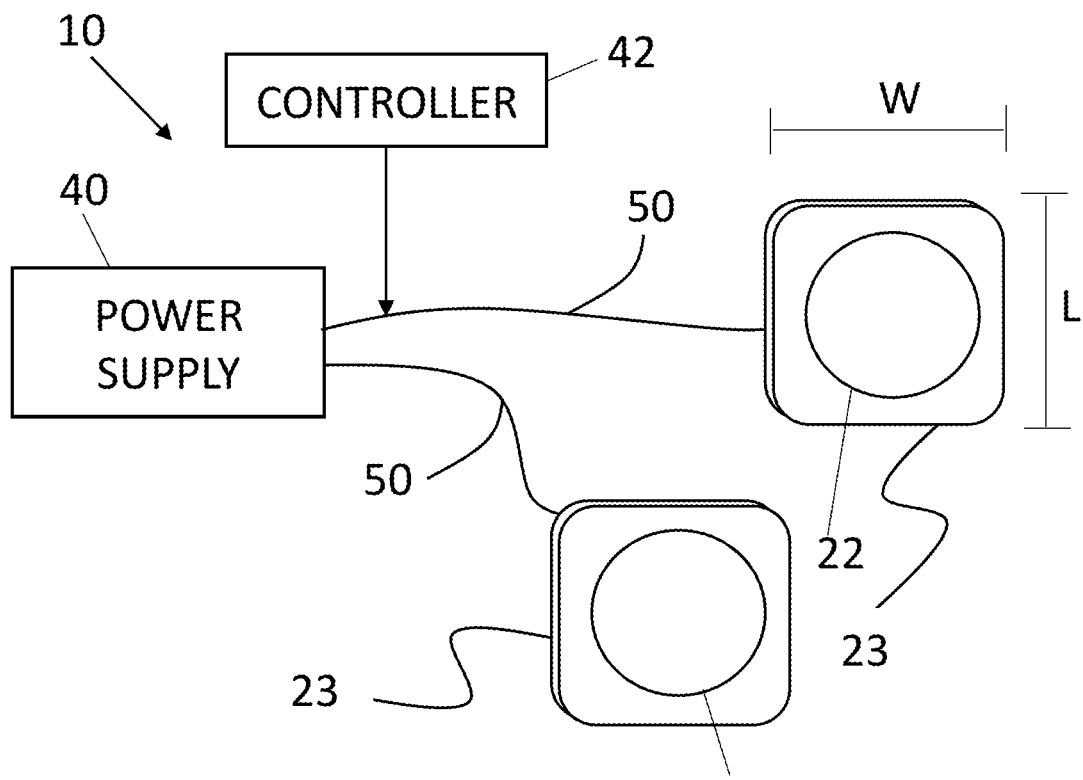
FIG. 1B depicts a schematic of a system for applying electric energy to a target area of a subject, according to some embodiments herein.

Disclosed herein are novel systems, devices, and methods useful for treatment of conditions of the skin and eyes. For example, systems, devices, and methods described herein can be used to treat or prevent skin conditions (e.g., diseases) caused by or associated with the presence of bacteria and/or the presence of biofilms in or around a target area of a subject, such as a skin surface (e.g., a skin surface of an eyelid or adjacent to an eyelid or eye). In some cases, systems, devices, or methods described herein can be used to treat (e.g., inhibit, disrupt, destroy, or remove) biofilms and/or pathogens associated with (e.g., contained within) biofilms, which can be exceedingly difficult to disrupt, destroy, or remove from a subject. In many cases, antibiotics, creams, and ointments cannot penetrate biofilms. As described herein, applying an electric current to a target area comprising a biofilm can lead to the destruction (e.g., vaporization) of a biofilm (and/or a pathogen within the biofilm, such as a bacteria) at a target area. For instance, subjecting a biofilm to a direct current of low amperage, e.g., at a voltage of at least 6 volts or more can destroy (e.g., vaporize) a biofilm. In some cases, a system, device, or method described herein can be used to treat or prevent a condition comprising or caused by debris, wherein the debris can include one or more of a biofilm, bacteria, scurf, keratinization, dead cells, or secreted fluids, for example, at a target area. In some cases, a target area of the present disclosure can comprise a skin surface. In some cases, a target area can comprise a skin surface of an eyelid (e.g., an upper eyelid and/or a lower eyelid) or a margin thereof (e.g., an upper eyelid margin or a lower eyelid margin), a skin surface adjacent to an eye or eyelid, or a gland, such as a skin gland. In some cases, a target area can comprise a surface of facial skin or of a skin of an extremity.

With reference to FIGS. 1A, 1B, 2A, and 2B and in accordance with some embodiments, devices 10 can be used to apply an electric current to, through, or across the skin of a subject. Application of the electric current to, through, or across a target area of a subject (e.g., a portion of the skin of a subject, for instance a portion of the surface of the skin) may cause a debris present on, within, or proximal to the target area to be removed, vaporized, or otherwise disrupted. Examples of debris can include, but are not limited to, biofilm, bacteria, scurf, keratinization, dead cells, and secreted fluids. In some cases, systems, methods, and devices 10 described herein can be used to apply electrical energy to prevent or treat a treatable condition (e.g., an infection or disease). Treatable conditions using the devices and method herein may include, but are not limited to, blepharitis, acne, snoring, razor bumps, nose zits, dry eye, and skin conditions associated with aging (e.g., dry skin, roughened skin, keratoses, or inflammation). In some embodiments, the devices and methods herein can reduce signs of aging caused by toxins produced by the bacteria/debris to be treated/removed by the devices and methods herein. In some embodiments, application of electrical energy (e.g., comprising an electrical signal) within proximity of a nasal cavity can reduce snoring. Removal of inflammatory toxins using the devices and methods herein may prevent the inflammatory toxins from reaching the posterior pharynx by sniffing or and swallowing, reduce or eliminate the low-grade inflammation and subsequent swelling associated with these toxins, which may thereby treat snoring conditions caused by such swelling and inflammation.

In some embodiments, a system or device 10 described herein includes one or more electrodes 20, 22. In some cases, the one or more electrodes may be placed in contact with (or adjacent to) a target area (e.g., a skin surface) to apply a low voltage and low current electrical energy through the skin. In some embodiments, the electrical current can be passed through the epidermis and/or the dermis region(s) at or proximal to a target area (e.g., by contacting one or more skin surfaces with the one or more electrodes and passing electrical energy through the electrodes). In some embodiments, electrical current can be passed through subcutaneous or hypodermis regions at or proximal to the target area (e.g., by contacting one or more skin surfaces with the one or more electrodes and passing electrical energy through the electrodes). An electrical current applied through the skin or to areas proximal to the skin surface at which the electrodes contact the skin may be additionally referred to as an electrical signal, an electrical energy, an electric signal, an electric current, or an electric energy, in some cases.

In some embodiments, electrical energy applied to a target area (e.g., by using one or more electrodes of a device described herein to pass the electrical energy through the skin) can disrupt or vaporize debris or biofilms. In some embodiments, disruption of debris can facilitate removal of the debris. In some cases, removal of debris (e.g., from a target area) can be facilitated by washing the target area with a wash solution or by wiping with a tissue or towel (e.g., after application of electrical energy to the target area by a device 10).

In many cases, electrical energy applied to a target area as described herein (e.g., via one or more electrodes) can be supplied by a power source and, optionally, regulated by a controller. In some embodiments, the voltage of the electrical energy applied can be about 0.1 V to about 25 V. In some embodiments, the voltage of the electrical energy applied to a target area (e.g., as supplied by the power source or as modulated by the controller) can be about 0.1 V to about 0.5 V, about 0.1 V to about 1 V, about 0.1 V to about 2 V, about 0.1 V to about 3 V, about 0.1 V to about 5 V, about 0.1 V to about 10 V, about 0.1 V to about 12 V, about 0.1 V to about 15 V, about 0.1 V to about 20 V, about 0.1 V to about 25 V, about 0.5 V to about 1 V, about 0.5 V to about 2 V, about 0.5 V to about 3 V, about 0.5 V to about 5 V, about 0.5 V to about 10 V, about 0.5 V to about 12 V, about 0.5 V to about 15 V, about 0.5 V to about 20 V, about 0.5 V to about 25 V, about 1 V to about 2 V, about 1 V to about 3 V, about 1 V to about 5 V, about 1 V to about 10 V, about 1 V to about 12 V, about 1 V to about 15 V, about 1 V to about 20 V, about 1 V to about 25 V, about 2 V to about 3 V, about 2 V to about 5 V, about 2 V to about 10 V, about 2 V to about 12 V, about 2 V to about 15 V, about 2 V to about 20 V, about 2 V to about 25 V, about 3 V to about 5 V, about 3 V to about 10 V, about 3 V to about 12 V, about 3 V to about 15 V, about 3 V to about 20 V, about 3 V to about 25 V, about 5 V to about 10 V, about 5 V to about 12 V, about 5 V to about 15 V, about 5 V to about 20 V, about 5 V to about 25 V, about 10 V to about 12 V, about 10 V to about 15 V, about 10 V to about 20 V, about 10 V to about 25 V, about 12 V to about 15 V, about 12 V to about 20 V, about 12 V to about 25 V, about 15 V to about 20 V, about 15 V to about 25 V, or about 20 V to about 25 V. In some embodiments, the voltage of the electrical energy applied can be about 0.1 V, about 0.5 V, about 1 V, about 2 V, about 3 V, about 5 V, about 10 V, about 12 V, about 15 V, about 20 V, or about 25 V. In some embodiments, the voltage of the electrical energy applied can be at least about 0.1 V, about 0.5 V, about 1 V, about 2 V, about 3 V, about 5 V, about 10 V, about 12 V, about 15 V, or about 20 V. In some embodiments, the voltage of the electrical energy applied can be at most about 0.5 V, about 1 V, about 2 V, about 3 V, about 5 V, about 10 V, about 12 V, about 15 V, about 20 V, or about 25 V.

In some embodiments, the current of the electrical energy applied to a target area (e.g., as supplied by a power supply or as modulated by a controller) can be about 0.1 milliamps to about 4 milliamps. In some embodiments, the current of the electrical energy applied can be about 0.1 milliamps to about 0.5 milliamps, about 0.1 milliamps to about 1 milliamps, about 0.1 milliamps to about 1.5 milliamps, about 0.1 milliamps to about 2 milliamps, about 0.1 milliamps to about 2.5 milliamps, about 0.1 milliamps to about 3 milliamps, about 0.1 milliamps to about 3.5 milliamps, about 0.1 milliamps to about 4 milliamps, about 0.5 milliamps to about 1 milliamps, about 0.5 milliamps to about 1.5 milliamps, about 0.5 milliamps to about 2 milliamps, about 0.5 milliamps to about 2.5 milliamps, about 0.5 milliamps to about 3 milliamps, about 0.5 milliamps to about 3.5 milliamps, about 0.5 milliamps to about 4 milliamps, about 1 milliamps to about 1.5 milliamps, about 1 milliamps to about 2 milliamps, about 1 milliamps to about 2.5 milliamps, about 1 milliamps to about 3 milliamps, about 1 milliamps to about 3.5 milliamps, about 1 milliamps to about 4 milliamps, about 1.5 milliamps to about 2 milliamps, about 1.5 milliamps to about 2.5 milliamps, about 1.5 milliamps to about 3 milliamps, about 1.5 milliamps to about 3.5 milliamps, about 1.5 milliamps to about 4 milliamps, about 2 milliamps to about 2.5 milliamps, about 2 milliamps to about 3 milliamps, about 2 milliamps to about 3.5 milliamps, about 2 milliamps to about 4 milliamps, about 2.5 milliamps to about 3 milliamps, about 2.5 milliamps to about 3.5 milliamps, about 2.5 milliamps to about 4 milliamps, about 3 milliamps to about 3.5 milliamps, about 3 milliamps to about 4 milliamps, or about 3.5 milliamps to about 4 milliamps. In some embodiments, the current of the electrical energy applied can be about 0.1 milliamps, about 0.5 milliamps, about 1 milliamps, about 1.5 milliamps, about 2 milliamps, about 2.5 milliamps, about 3 milliamps, about 3.5 milliamps, or about 4 milliamps. In some embodiments, the current of the electrical energy applied can be at least about 0.1 milliamps, about 0.5 milliamps, about 1 milliamps, about 1.5 milliamps, about 2 milliamps, about 2.5 milliamps, about 3 milliamps, or about 3.5 milliamps. In some embodiments, the current of the electrical energy applied can be at most about 0.5 milliamps, about 1 milliamps, about 1.5 milliamps, about 2 milliamps, about 2.5 milliamps, about 3 milliamps, about 3.5 milliamps, or about 4 milliamps.

In some embodiments, the current can be applied as direct current (DC). In some embodiments, the current can be applied as an alternating current (AC). In some embodiments, the current can be applied in a sequence which includes alternating AC and DC currents, fluctuations in current amplitude, changing of AC current waveforms, and combinations thereof.

In some embodiments, the device 10 for applying an electrical signal can include at least a first electrode 20 and a second electrode 22. In some embodiments, a surface of the electrodes 20,22 can be configured to be adhered to a skin surface. In some embodiments, the surface of the electrodes which adhere to the skin surface can comprise a gel adhesive. The adhesive may allow for repeated placements of the electrodes onto the skin surface. In some embodiments, a surface of the electrode 20, 22 can be curved to generally correspond to the external curvature of a skin surface. In some embodiments, the first and second electrodes can be provided on separate surfaces, allowing a user to control the spacing between the electrodes. Each of the first and second electrodes 20, 22 may have a width W and a length L. In some cases, an adhesive pad may have a width W and a length L. In some embodiments, each of the first and second electrodes 20, 22 are the same size in area. In some embodiments, each of the first and second electrodes 20, 22 are a different size in area. In some embodiments, the one or more of the electrodes or one or more of the adhesive pads are substantially square having a width W approximately equal to the length L. In some embodiments, the one or more of the electrodes or one or more of the adhesive pads are substantially rectangular having a length L larger than the width W. In some cases, one or more electrodes or one or more adhesive pads are substantially circular, having a width W equal to a diameter of the electrode or pad. In some cases, one or more electrodes or one or more adhesive pads are substantially elliptical, having a length L equal to a major axis of the ellipse and a width W equal to a minor axis of the ellipse. In some cases, the width W of an electrode can be 0.1 cm to 0.25 cm, 0.25 cm to 0.5 cm, 0.5 cm to 1.0 cm, 1.0 cm to 1.5 cm, 1.5 cm to 2.0 cm, 2.0 cm to 2.5 cm, 2.5 cm to 3.0 cm, 3.0 cm to 4.0 cm, 4.0 cm to 5.0 cm, or greater than 5.0 cm. In some cases, the length L of an electrode can be 0.1 cm to 0.25 cm, 0.25 cm to 0.5 cm, 0.5 cm to 1.0 cm, 1.0 cm to 1.5 cm, 1.5 cm to 2.0 cm, 2.0 cm to 2.5 cm, 2.5 cm to 3.0 cm, 3.0 cm to 4.0 cm, 4.0 cm to 5.0 cm, or greater than 5.0 cm. Electrodes and/or pads may be provided in various sizes and shapes (e.g., shaped to cover an eye or a portion thereof, such as an eyelid). Electrode or pad shapes may include square, circular, elliptical, oval, butterfly, curved and peanut shaped outlines. In some cases, an electrode or pad can be shaped to conform to a shape of a target area or a body part of the subject (e.g., an eye).

In some embodiments, a voltage differential between the first and second electrodes may produce the electrical current which travels between the electrodes and to areas of the skin proximal to the sites at which the electrodes contact the skin surface. In some embodiments, a voltage differential between an electrode and the skin itself may produce the electrical current which travels to areas of the skin proximal to the sites at which the electrodes contact the skin surface. In some embodiments, one of the first electrode or second electrodes 20, 22 may function as a cathode and the other of the first electrode or second electrodes 20, 22 may function as an anode. In some embodiments, first and second electrodes 20, 22 can be electrically coupled to a circuit that may include a power supply 40 via one or more wire leads 50.

In some embodiments, the device can include a power supply 40, e.g., wherein the power supply is configured to supply electrical energy to the one or more electrodes. The device may also include hardware, software, or any combination thereof that may be used to control the electrical energy being supplied to the electrodes. The hardware, such as a controller 42, may include software and be electrically coupled to the power supply 40 and the electrodes. Embodiments of the device may also include instructions supplied by a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical optical, acoustical or other forms of propagated signals (e.g., carrier waves, infrared signals, digital signals, etc.), and others. Further software routines and instructions may be described herein as performing certain actions. However, it should be appreciated that such descriptions are merely for convenience and that such actions in fact result from computing devices, processors, controllers 42, or other devices executing the software, routines, instructions, etc.

In some embodiments, the controller can include a feedback circuit. The feedback circuit may be utilized to control parameters of the electrical signal being produced by the electrodes. In some embodiments, electrical output at the electrode can be used as input into the feedback loop. In some embodiments, voltage and/or current at one of the electrodes can be used as input into the feedback loop. The feedback input may be utilized by the controller to determine parameters such as resistivity of the skin at which the electrical signal is applied, actual current applied through the skin, and actual voltage applied through the skin. In some embodiments, the feedback loop can adjust the electrical signal to maintain safe levels of voltage and current being supplied to the skin by the electrodes. In some embodiments, the feedback circuit ensures that can adjust the electrical signal such that is effective over a number of variable, such as various skin types or ambient conditions such as humidity of the environment. In some embodiments, the feedback circuit can be a positive feedback circuit. In some embodiments, the feedback circuit can be a negative feedback circuit.

In some embodiments, the device 10, may include a controller 42 comprising a user interface that includes an input system and a display system. The input system allows the user to adjust the operation of the device 10, and, in some embodiments, interact with the controller 42 to control the device. For example, the user interface may allow the user to activate the supply of electrical energy to the electrodes 20, 22, to increase or decrease the electrical energy being supplied to the electrodes 20, 22, increase or decrease the duration of treatment, and combinations thereof.

Figure 2A:
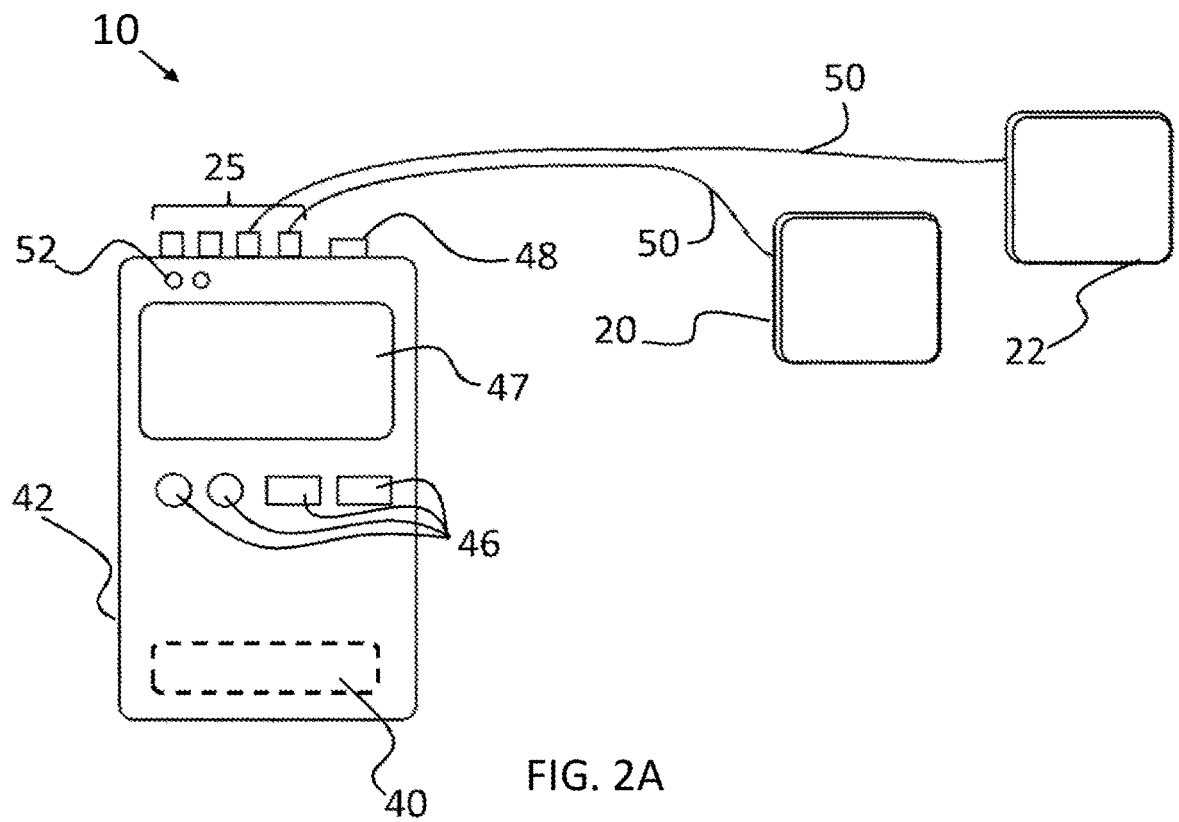
FIG. 2A depicts a system for applying electric energy to a target area of a subject, according to some embodiments herein.
Figure 2B:
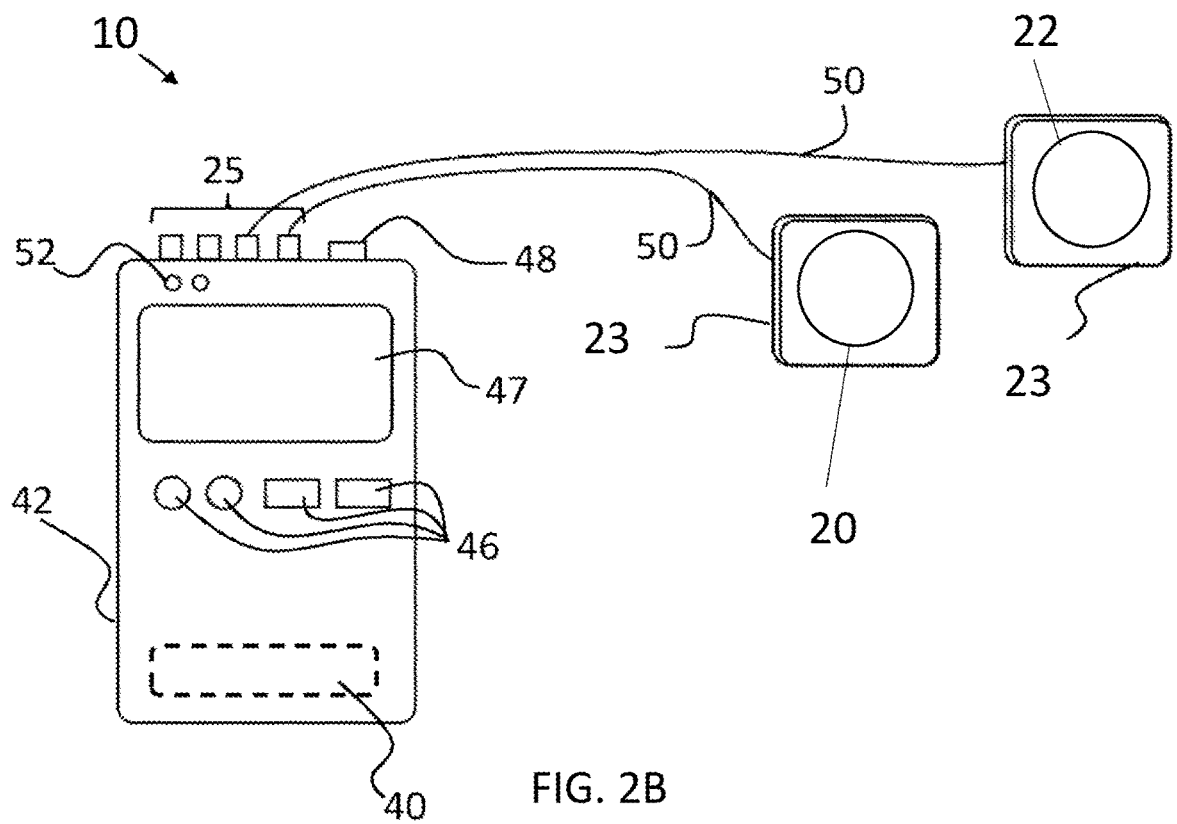
FIG. 2B depicts a system for applying electric energy to a target area of a subject, according to some embodiments herein.

With reference to FIG. 2A and FIG. 2B, the input system may include at least one of a button 46, a dial 48, a trigger, a switch, a touch screen, and/or other input devices as are known in the electrical arts. A display system may convey information to the user with respect to the status of the device. In some embodiments, the display may include one or more lights 52 such as light emitting diodes, an LCD display 47, gauges, or other types of displays as are known in the art. For example, the controller 42 may include one or more lights 52 to indicate the powered on status of the device, indicate the level of energy remaining in the power supply, such as in a battery, or if the electrodes are making sufficient contact with the skin of the subject undergoing treatment.

In some embodiments, as depicted by FIG. 2A and FIG. 2B, the controller 42, power supply 40, and user interface (e.g., lights 52 and buttons 46) are contained in a housing. It will be appreciated that the controller, power supply, user interface, and other components may be in one or more housings and the one or more housings. A housing with one or more components may be a base unit that can be located some distance away from the subject but that is also electrically coupled to the skin contacting portion by a flexible member, such as an electric cable.

In some embodiments, the controller comprises a plurality of electrode outputs 25. In some embodiments, each output 25 is labeled as a positive or negative output. In some embodiments, each output is labeled as a cathode or anode output. The outputs 25 may be colored corresponding to the electric polarity (i.e. red for positive and black for negative or vice versa). In some embodiments, the polarity of the output 25 is selected using the controller.

As depicted in FIGS. 2B, 3A, 3D, and 3E, one or more electrodes 20, 22 may be included on a single pad 23. In some embodiments, the pad 23 can be configured to be placed on a specific skin surface. In some embodiments, wherein the device can be configured to treat a snoring condition, the pad 23 can be shaped similar to a nasal strip or butterfly strip. In some embodiments, the pad 23 can be adhered to a nose of a user, such that the first electrode 20 is placed on a first side of the nose, and the second electrode 22 can be placed on the opposite of the nose, with the narrow region being placed across the bridge of the nose.

In some embodiments, providing one or more electrodes on a single pad fixes the distance between the electrodes. Fixing the distance between a first electrode 20 and a second electrode 22 may reduce chances of misplacement and improve the efficacy of the device. In some embodiments, each electrode 20, 22 of the pad can be connected to a separate lead wire 50. In some embodiments, the lead wires 50 can be connected to outputs of a controller (e.g. outputs 25 of controller 42 as depicted by FIG. 2A and FIG. 2B).

Figure 3A:
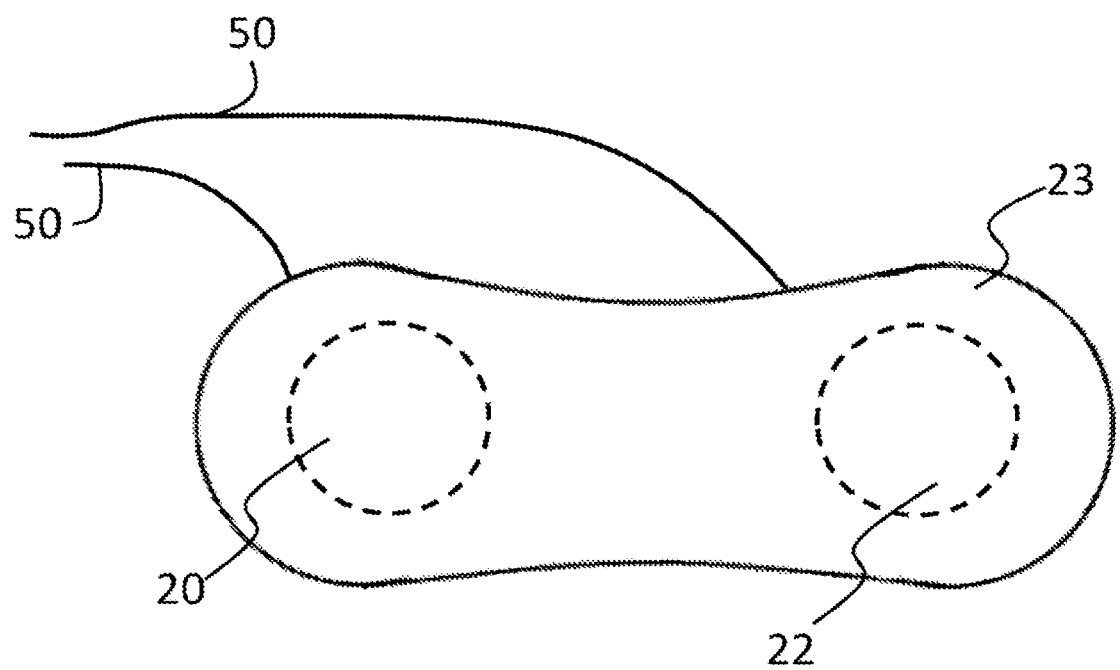
FIGS. 3A, 3B, 3C, 3D and 3E depict components of systems and devices useful for applying electric energy to a target area of a subject, according to some embodiments herein.
Figure 3B:
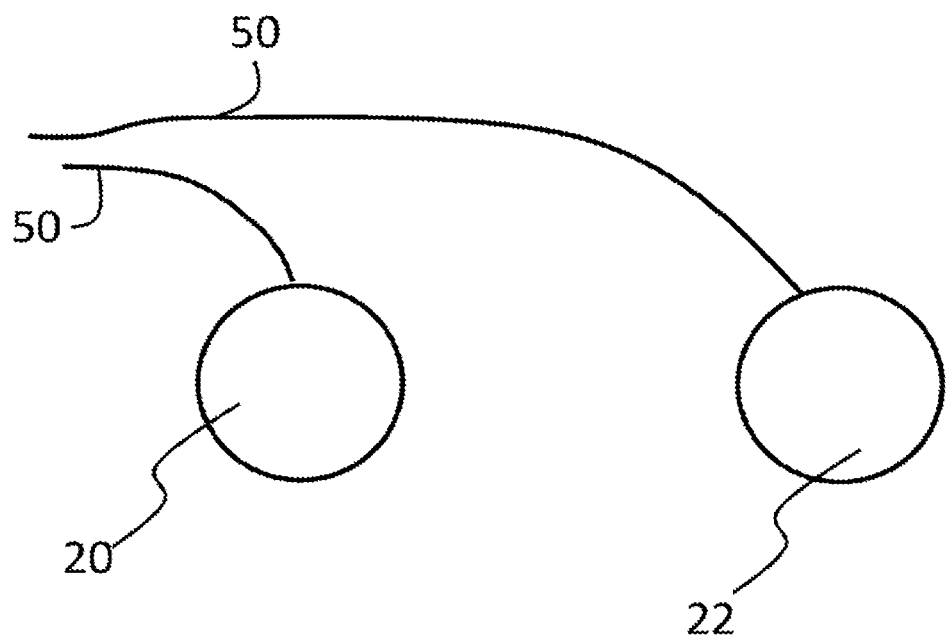
Figure 3C:
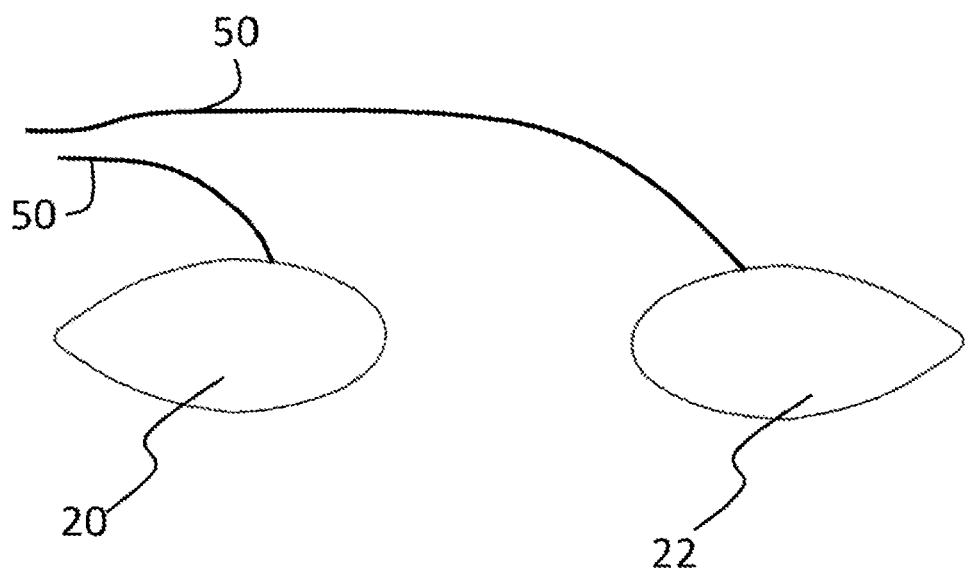
Figure 3D:
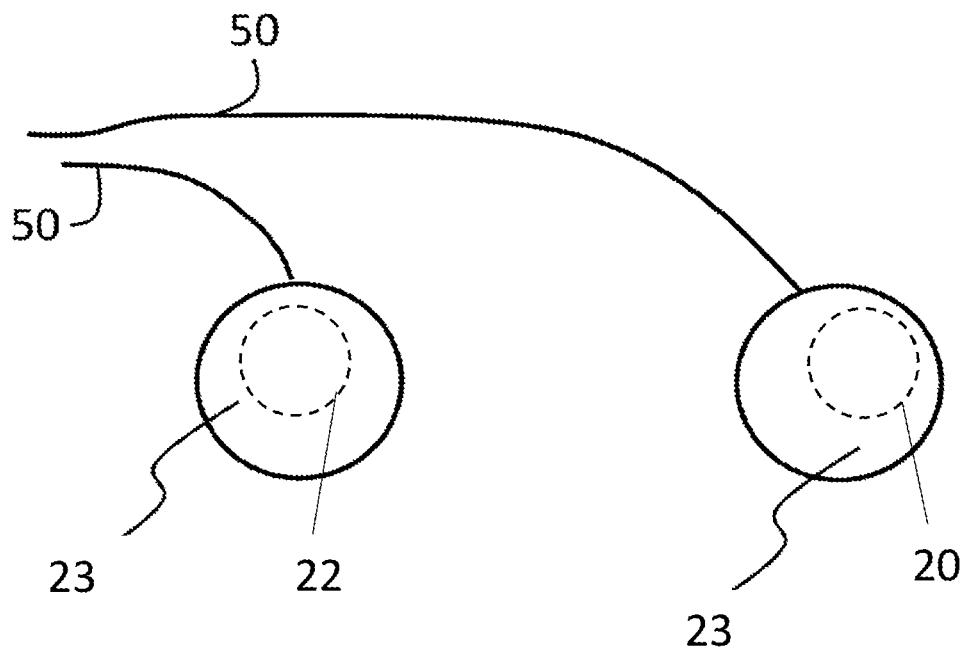
Figure 3E:
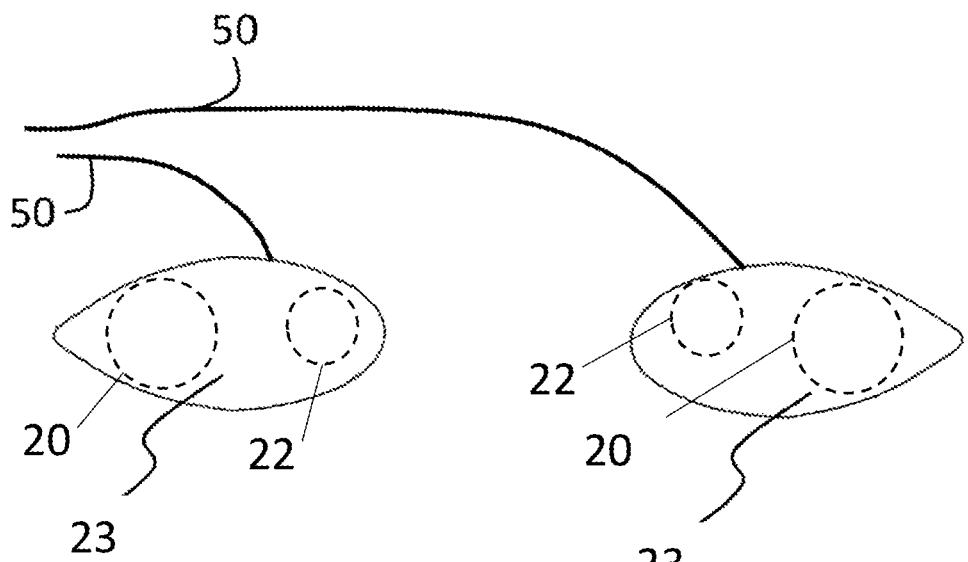

In some embodiments, the electrode pads can be configured to surround the mouth to vaporize intra-oral biofilm. In some embodiments, the electrode pads can be configured to adhere to the eyelids to vaporize biofilm along the eyelid margins. As depicted in FIG. 3C and FIG. 3E, electrode pads to be placed on the eyelids may comprise two teardrop or almond-shaped electrodes 20,22 or electrode pads 23.

Secondary benefits of electrical therapy applied to the skin may include reduction of blepharitis (inflammation of the eyelids caused by virulence factors), acne inside the nose, and acne on the face. Reduction of acne on the face may be enhanced by using pads on the cheek areas. Electrical therapy may reduce the signs of aging by reducing the amount of virulence factors which are swallowed on a daily basis.

In some embodiments, a solution may be applied to the skin to reduce an electrical resistivity or impedance of the skin. In some embodiments, the solution is an electrolyte solution. In some embodiments, the solution is applied to the skin to improve the disruption of debris by the electrical energy.

Pads

A system, device, or method described herein can comprise one or more pads 23. A pad 23 described herein can be configured to contact a target area (e.g., an affected skin surface) or a region adjacent to a target area. A pad 23 (e.g., an adhesive pad) can comprise an adhesive or other agent for placing the pad 23 or component thereof (e.g., one or more electrodes of the pad 23) in contact with or in proximity to a target area (e.g., a skin surface of a subject). In some cases, an adhesive can be a gel, a glue, or a viscous fluid. In some cases, an adhesive can be electrolytic. For example, an adhesive can facilitate transmission of electrical energy to a target area, in some cases.

In many cases, a pad 23 can comprise one or more electrodes, for example, wherein the one or more electrodes are connected to a power supply and/or a controller (e.g., via one or more wires). An electrode of a pad 23 can be used to deliver electrical energy to a target area (e.g., a skin surface of a subject). In some cases, a pad 23 can comprise an electrically non-conductive material coupled to one or more electrodes. In some cases, a pad 23 can be coupled to a plurality of electrodes. In some cases, a pad 23 can be coupled to an anode electrode and a cathode electrode. In some cases, a pad 23 can be coupled to an anode electrode and a second pad 23 can be coupled to a cathode electrode (e.g., wherein the anode electrode and cathode electrode are electrically connected to a power supply and/or a controller of a system, devices, or method described herein).

In many cases, a system, device, or method described herein comprises a plurality of pads 23. For instance, a system, device, or method described herein can comprise a first pad 23 for contacting a first target region (e.g., a target region on a first eye or eyelid of a subject) and a second pad 23 for contacting a second target region (e.g., wherein the second target region is on or adjacent to a second eye or eyelid of the subject).

In some cases, a pad 23 can be applied to a target area of a subject in need of treatment. In some cases, a first pad 23 can be coupled to (e.g., adhered to) a first region of a target area and a second pad 23 coupled to a second region of the target area. In some cases, a first pad 23 can be coupled to (e.g., adhered to) to a first region adjacent to a target area and a second pad 23 can be coupled to a second region adjacent to the target area.

Controllers

A system, device, or method described herein can comprise a controller. A controller can be connected to a power supply (e.g., via one or more wires) and/or to one or more electrodes (e.g., one or more electrodes of one or more pads 23 described herein). A controller can comprise a processor, a memory, and/or a user interface. A memory (e.g., a non-transitory memory) of a controller can comprise instructions that, when executed, can cause the processor to perform one or more steps of a method described herein. For instance, a controller can be configured to modulate an electrical signal from a power supply. In some cases, a controller can be configured to modulate an amplitude (e.g., a current amplitude or a voltage amplitude) of electrical energy (e.g., provided by a power supply), which may be transmitted to one or more electrodes (e.g., via wires 50) for application to a target area. In some cases, a controller can be configured to modulate a frequency (e.g., of a current or voltage) of electrical energy (e.g., provided by a power supply), which may be transmitted to one or more electrodes (e.g., via wires 50) for application to a target area. In some cases, electrical energy modulated by a controller can comprise an electrical signal (e.g., comprising a waveform). In some cases, applying electrical energy in the form of an electrical signal (e.g., comprising a waveform) to a target area (e.g., via one or more electrodes) can improve prevention or treatment of a target area, as described herein, in some embodiments.

In many cases, electrical energy can be applied (e.g., in the form of a voltage drop between two electrodes on separate adhesive pads or in the form of a voltage drop across two electrodes in a single adhesive pad) to a target area (e.g., a skin surface of a subject) without the delivery of another form of energy to the target area. For example, delivery of electrical energy to a target area using systems, devices, and methods described herein can be sufficient for treating or preventing a condition described herein (e.g., without application of another form of energy to the target area during the practice of the system, device, or method). In some embodiments, ultrasonic energy can be applied without the application of any other form of energy to disrupt debris. In some cases, electrical energy can be administered to a target area (e.g., a skin surface of an eye) using a system, device, or method described herein while another form of energy (e.g., ultrasonic energy) may be applied to the target region (e.g., via an adhesive pad described herein). In some cases, a treatment of a subject can comprise applying electrical energy and another form of energy to the target area at different times. In some cases, a treatment of a subject can comprise applying only electrical energy to the target area. In some cases, electrical energy and the other form of energy, such as ultrasonic energy, may be applied in an alternating manner, or one of these forms of energy may be applied first and the other form of energy may be applied second. This alternating pattern may be repeated. In an embodiment, the other form of energy, such as ultrasonic energy, can be applied first and the electrical energy can be applied second. In another embodiment, the electrical energy can be applied first and the other form of energy, such as ultrasonic energy, can be applied second. The electrical energy can be applied for a duration and at a frequency sufficient to disrupt debris (e.g., biofilm) on the eyelid, and in particular debris (e.g., biofilm) on the eyelid margin.

Figure 4:
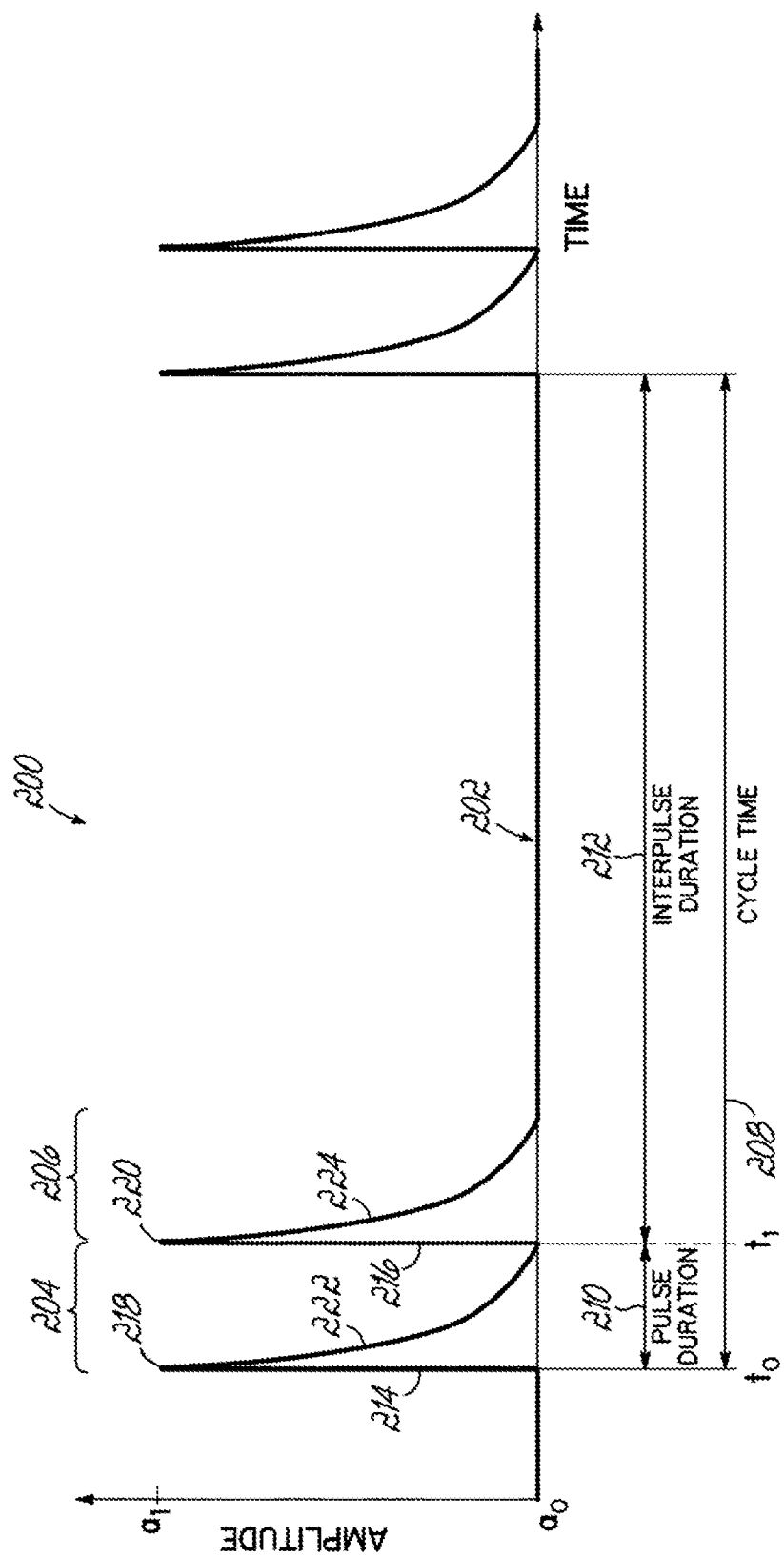
FIG. 4 depicts an example of a twin peak monophasic waveform, in accordance with embodiments of devices, systems, and methods described herein.

FIG. 4 depicts a graph 200 that shows an exemplary monophasic waveform 202 which may be used to provide electrical energy to an eye contacting portion (e.g., comprising a pad 23 and/or one or more electrodes 20, 22) of device 10. The monophasic waveform 202 may include a plurality of pulses (e.g., an initial pulse 204 and subsequent pulse 206) that repeat over a cycle time 208 and which can be used to electrolytically disrupt debris on an eyelid margin. Each pulse 204, 206 may have a pulse duration 210 and an interpulse duration 212 that collectively define the cycle time 208 of monophasic waveform 202. Each pulse 204, 206 may have a relatively short rise time 214, 216 during which the amplitude of the monophasic waveform 202 rises from an initial baseline amplitude a0 (e.g., zero volts or amps) to a peak 218, 220 having a peak amplitude a1, and fall time 222, 224 during which the amplitude of the monophasic waveform 202 falls back toward the baseline amplitude a0, e.g., by decaying at a generally exponential rate.

Prior to time t0, the monophasic waveform 202 may be at the initial baseline amplitude a0. At the beginning of the cycle time 208, the amplitude of the monophasic waveform may begin rising and reach the initial peak 218 in a relatively short period of time, e.g., 1 μs. After reaching the initial peak 218, the amplitude of the monophasic waveform 202 may drop back toward the baseline amplitude a0 over a period of time. The drop in the amplitude may be exponential in nature as the electrical energy dissipates into the patient. The period between peaks 218, 220 may be selected to allow the amplitude of the monophasic waveform to essentially return to the baseline amplitude a0 before generating subsequent peak 220. At time t1, the amplitude of the monophasic waveform 202 may begin to rise to subsequent peak 220, which may have the same amplitude a1 as the initial peak 218. The amplitude of the monophasic waveform may then drop back toward the baseline amplitude a0 over a period of time in similar manner as described for the initial peak 218. After the final pulse of the plurality of pulses, the monophasic waveform 202 may remain at baseline amplitude a0 for the remainder of cycle time 208.

The amplitude of the monophasic waveform 202 may be characterized using current or voltage so that the baseline amplitude a0 is zero volts or amps. For peaks 218, 220 characterized by voltage, the peak amplitude a1 may be approximately 350 V. For peaks 218, 220 characterized by current, the peak amplitude a1 may be approximately 700 mA. An exemplary monophasic waveform 202 may have a cycle time 208 of approximately 10 ms and a pulse duration 210 of approximately 0.2 ms.

Figure 5:
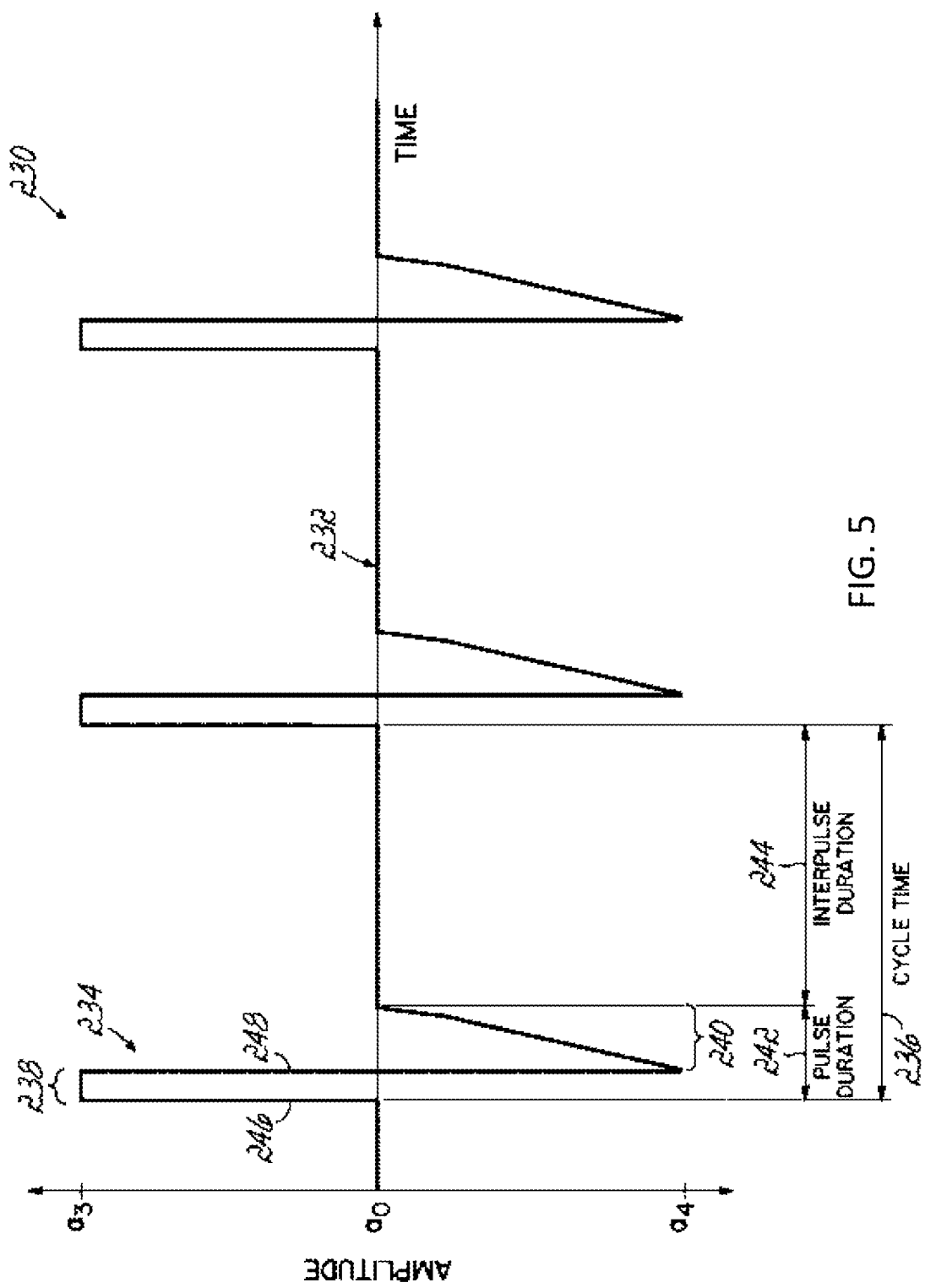
FIG. 5 depicts an example of a biphasic asymmetrical waveform, in accordance with embodiments of devices, systems, and methods described herein.

FIG. 5 depicts a graph 230 that shows an exemplary biphasic waveform 232 that may be used to provide electrical energy to the eye contacting portion (e.g., comprising an adhesive pad and/or one or more electrodes) of device 10. The biphasic waveform 232 may be asymmetric, and may include a pulse 234 that repeats over a cycle time 236 and which can be used to electrolytically disrupt debris on an eyelid margin. Each pulse 234 may include a positive phase 238, a negative phase 240, and a pulse duration 242. The pulse duration 242 and an interpulse duration 244 may collectively define the cycle time 236 of biphasic waveform 232.

The positive phase 238 of pulse 234 may have a relatively short rise time 246 (e.g., 1 microseconds (μS) during which the amplitude of the biphasic waveform 232 rises from the initial baseline amplitude a0 to a positive peak amplitude a3, and relatively short fall time 248 during which the amplitude of the biphasic waveform 232 falls toward a negative peak amplitude a4. In an embodiment of the invention, the positive peak amplitude a3 may have about the same magnitude as the negative peak amplitude a4. The positive phase 238 may comprise a portion (e.g., about a third) of the pulse 234 during which the amplitude of biphasic waveform 232 is held at the positive peak amplitude a3. During the negative phase 240 of pulse 234, the amplitude of the biphasic waveform 232 may decay or be driven toward the baseline amplitude a0 at a generally linear rate from the negative peak amplitude a4 back toward the baseline amplitude a0 over the remaining portion of the pulse duration 242.

The amplitude of the biphasic waveform 232 may also be characterized using current or voltage. In cases where the biphasic waveform 232 is characterized by voltage, the peak amplitude a5 may be in a range of approximately 0 to +50V, and the peak amplitude a4 may be in a range of approximately 0 to −50V. In cases where the biphasic waveform 232 is characterized by current, the peak amplitude a5 may be in a range of approximately 0 to +100 mA, and the peak amplitude a4 may be in a range of approximately 0 to −100 mA. An exemplary biphasic waveform 232 may have a pulse duration 242 in a range of approximately 50 to 300 μs, and may be user adjustable in increments, e.g., 10 μs increments. The exemplary biphasic waveform may further include a cycle time 236 in a range of approximately 6.67 to 500 ms, yielding a frequency of 2-150 Hz, and may be adjustable in increments of frequency, e.g., 1 Hz increments.

Figure 6:
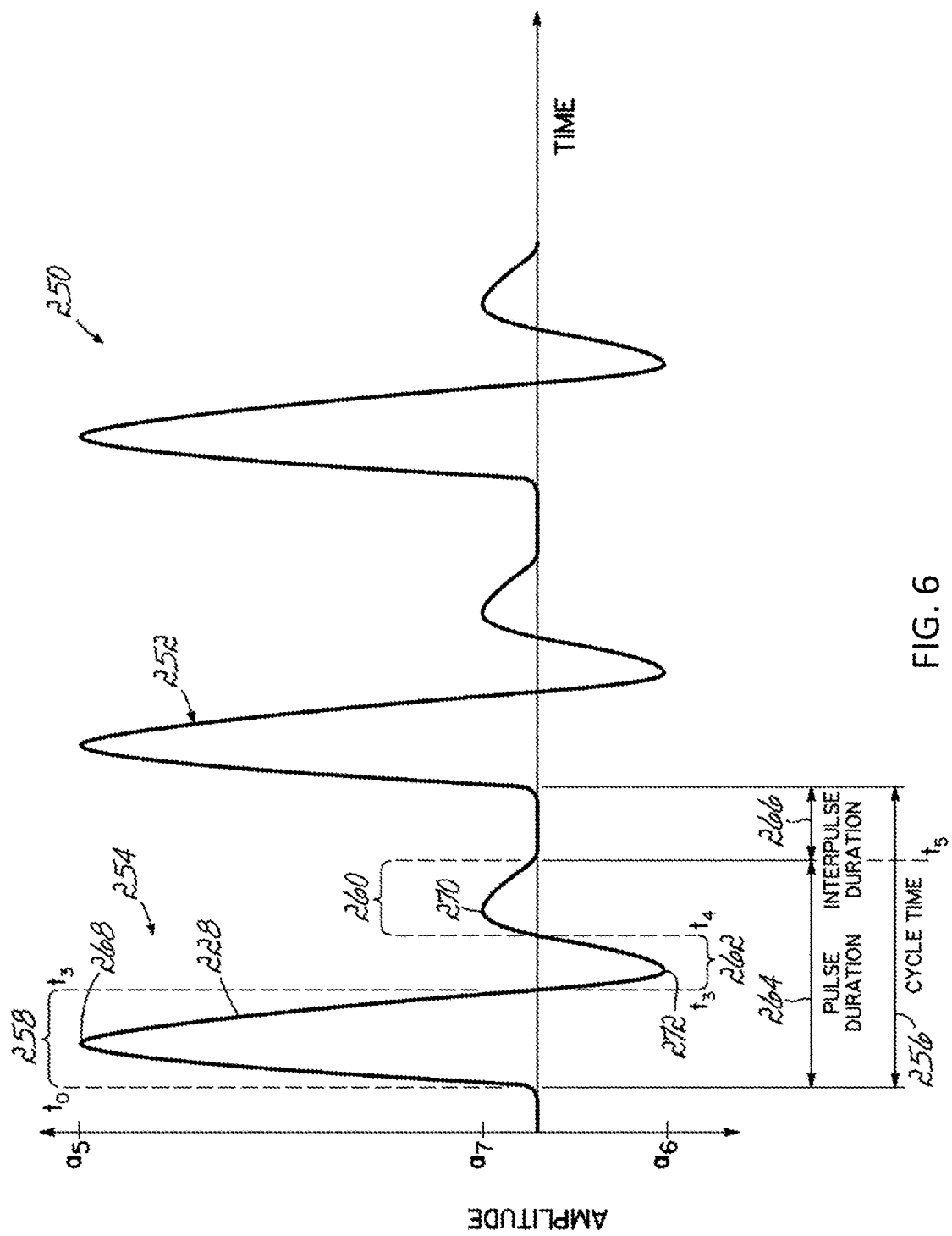
FIG. 6 depicts an example of an unbalanced triphasic waveform, in accordance with embodiments of devices, systems, and methods described herein.

FIG. 6 depicts a graph 250 that shows an exemplary triphasic waveform 252 that may be used to provide electrical energy to the eye contacting portion (e.g., comprising a pad and/or one or more electrodes) of device 10. The triphasic waveform 252 may include a pulse 254 that repeats over a cycle time 256 and which can be used to electrolytically disrupt debris on an eyelid margin. Each pulse 254 may include two positive phases 258, 260, a negative phase 262, and a pulse duration 264. The pulse duration 264 and an interpulse duration 266 may collectively define the cycle time 256 of triphasic waveform 252.

The initial positive phase 258 may have a peak 268 that predominates over peak 270 of subsequent positive phase 260 and over peak 272 of negative phase 262. That is, the amplitude a5 of peak 268 may be greater than the amplitudes a6, a7 of the subsequent peaks 270, 272. Each of the phases 258, 260, 262 may have a generally sinusoidal shape with peak amplitudes a5, a6, a7 that follow a generally exponential decay rate as compared to the preceding peaks 268, 270, 272.

Prior to time t0, the triphasic waveform 252 may initially be at the baseline amplitude a0. At the beginning of the cycle time 256, the amplitude of the triphasic waveform 252 may rise to positive peak 268 following a generally sinusoidal curve. The amplitude of the triphasic waveform 252 may then drop below the baseline amplitude a0 over a period of time following a generally sinusoidal curve to reach negative peak 272 between zero-crossing times t3 and t4. The amplitude of the triphasic waveform 252 may then begin to rise above the baseline amplitude a0 over a period of time following a generally sinusoidal curve to reach positive peak 270 between zero-crossing times time to and t5. Each peak 270, 272 may have a reduced magnitude in comparison to the magnitude of the immediately preceding peak 268, 270. After reaching peak 270, the amplitude of the triphasic waveform 252 may drop toward the baseline amplitude a0 over a period of time and remain there for the remainder of cycle time 256.

Figure 7:
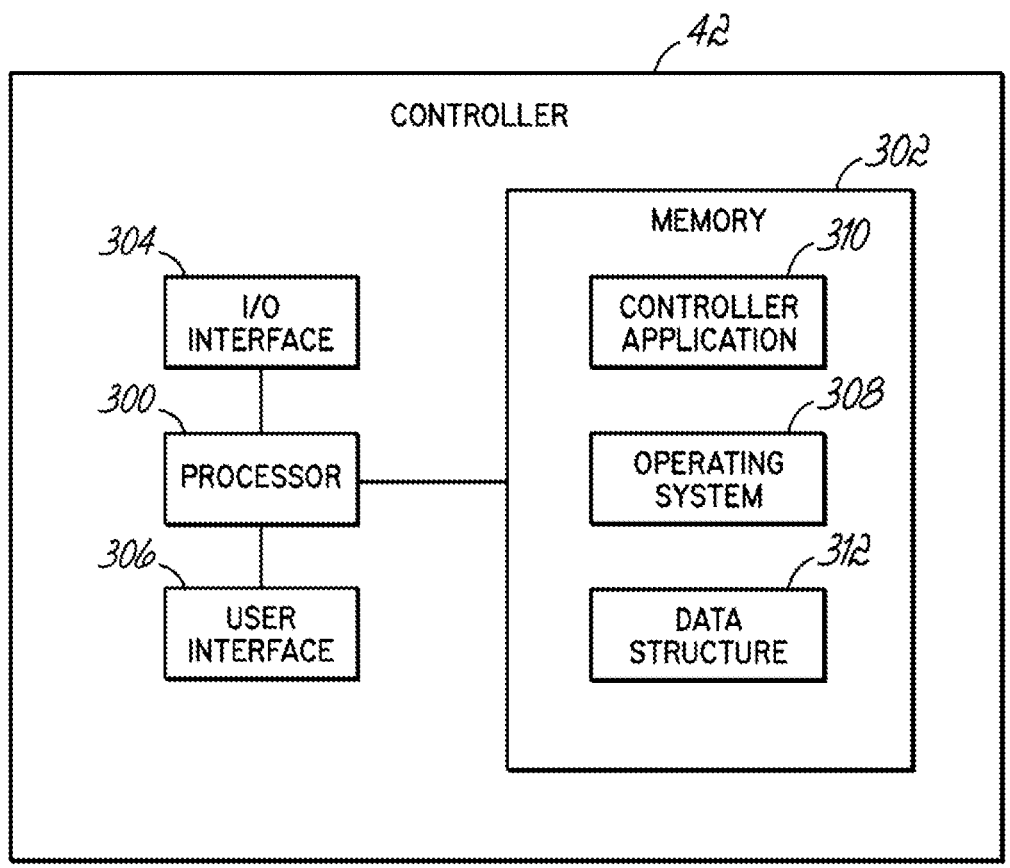
FIG. 7 is a schematic representation of a controller, in accordance with embodiments of devices, systems, and methods described herein.

FIG. 7 depicts an exemplary controller 42 in accordance with an embodiment of the invention. The controller 42 may include a processor 300, a memory 302, an input/output (I/O) interface 304, and a user interface 306. The processor 300 may include one or more devices selected from microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on operational instructions that are stored in the memory 302. Memory 302 may be a single memory device or a plurality of memory devices including but not limited to read-only memory (ROM), random access memory (RAM), volatile memory, non-volatile memory, static random access memory (SRAM), dynamic random access memory (DRAM), flash memory, cache memory, or any other device capable of storing digital information. Memory 302 may also include a mass storage device (not shown) such as a hard drive, optical drive, tape drive, non-volatile solid state device or any other device capable of storing digital information.

Processor 300 may operate under the control of an operating system 308 that resides in memory 302. The operating system 308 may manage controller resources so that computer program code embodied as one or more computer software applications, such as a controller application 310 residing in memory 302 may have instructions executed by the processor 300. In an alternative embodiment, the processor 300 may execute the controller application 310 directly, in which case the operating system 308 may be omitted. One or more data structures 312 may also reside in memory 302, and may be used by the processor 300, operating system 308, and/or controller application 310 to store data.

The I/O interface 304 may operatively couple the processor 300 to other components of embodiments of the invention, such as electrodes 20, 20 a, 20 b, 20 c, 22, 22 a, 22 b, 22 c, 24, 24 a, 26, 26 a, pump 100, and/or vacuum pump 101. The I/O interface 304 may include signal processing circuits that condition incoming and outgoing signals so that the signals are compatible with both the processor 300 and the components to which the processor 300 is coupled. To this end, the I/O interface 304 may include analog-to-digital (A/D) and/or digital-to-analog (D/A) converters, voltage level and/or frequency shifting circuits, optical isolation and/or driver circuits, and/or any other analog or digital circuitry suitable for coupling the processor 300 to the other components of embodiments of the invention.

The user interface 306 may be operatively coupled to the processor 300 of controller 42 in a known manner to allow a system operator to interact with the controller 42. The user interface 306 may include a display such as a video monitor, alphanumeric displays, a touch screen, a speaker, and any other suitable audio and visual indicators capable of providing information to the system operator. User interface 306 may also include input devices and controls such as an alphanumeric keyboard, a pointing device, keypads, pushbuttons, control knobs, microphones, etc., capable of accepting commands or input from the operator and transmitting the entered input to the processor 300. In this way, user interface 306 may enable manual initiation or selection of system functions, for example, during system set-up, calibration, and chemical loading.

Applications

Among the causes thought to play a role in many chronic conditions of the skin and/or eyes is the formation of biofilms in the environment of the eye. Such causes may play a role in the formation and/or development of teenage acne and Acne Rosacea. Bacteria that produce biofilms, mainly Staph *aureus* and Staph *epidermidis*, are still present in vast numbers. Structures of the body can retain moisture, which can provide a niche for growth of bacteria, including those that produce biofilms such as Staph *aureus* and Staph *epidermidis*, within the skin (e.g., various sweat and sebaceous glands). During adolescence, when the hormonal balances are changing, sweat and sebum may be overproduced and provide a very moist environment. This moist environment may allow for bacteria to produce biofilm. It is highly likely that during this time of adolescence thin biofilms develop on the face, since this is the area of most glandular activity. The biofilm may slowly creep into the glands and within the biofilm, bacteria may begin producing toxins. These toxins may lead to inflammation within the glands, known as teenage acne. As the hormones stabilize, normal rapid cellular turnover of youth tends to eliminate the glands with biofilm, and complexion returns to normal. Systems, devices, and methods described herein can be useful in treating or preventing pathogens such as bacteria and/or biofilms from persisting in or on a subject's skin.

The overall production of virulence factors on all warm moist surfaces above the neck may cause one or more of several different maladies which can be treated or prevented by the systems, devices, and methods described herein, not just acne. The disease or condition to be treated may depend on where the electrode pads are placed. The biofilms in all of these locations eventually send the virulence factors they produce to the posterior pharynx area via swallowing or sniffing. Virulence factors may travel through the nasolacrimal duct to the posterior sinuses and to the posterior pharynx by swallowing. The toxins may contact the posterior pharynx where they induce a small amount of inflammation which causes slight edema to occur, resulting in snoring. In some embodiments, the electrode pads are configured to be placed on the nose to vaporize biofilm within the nasal and sinus cavities and treat a snoring condition. As depicted in FIG. 3B and FIG. 3D, electrode pads 20, 22 to be placed on the nose may comprise two round or substantially circular electrode pads. In some embodiments, the electrode pads are placed on opposite sides of the nose. The electrode pads may comprise various shapes and may vaporize biofilm, thereby reducing the virulence factors, decreasing toxins which are passed to the posterior pharynx. Even the slightest edema within the posterior pharynx can cause a close approximation of the walls of this area causing air movement to flutter these walls open and closed causing the sound of snoring.

In older adults the mechanism may be slightly different. Accumulation of biofilm within the facial glands occurs not because of a burst of hormonal activity, but because of age. The bacteria have more years to finally gain a microscopic foothold in the facial glands, and very slowly the biofilm may begin to accumulate. It can be much slower than in the mouth or on the eyelids because there is much less moisture, however, once biofilm captures an area it seldom gives it up. With the slower cellular turnover of adults, and the affected glands acting as reservoirs for further biofilm advancement and accumulation, inflammation on the face may show up along with telangiectatic vessels causing a condition referred to as Acne rosacea. This disease has proven extremely hard to treat, since the biofilm cannot be removed. Compounds such as retinol can increase cell turnover, and sometimes improve signs and symptoms, but any relief is typically short lived if not accompanied by additional therapy capable of removing the biofilm, such as the use of a system, device, or method described herein (e.g., comprising application of electrical energy to an affected target area).

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The terms "subject," "individual," or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some cases, the subject is not necessarily diagnosed or suspected of being at high risk for the disease.

As used herein, the term "about" a number refers to that number plus or minus 10% of that number. The term "about" a range refers to that range minus 10% of its lowest value and plus 10% of its greatest value.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

The section headings used herein are for organizational purposes only and are not to be construed as limiting the subject matter described.

The invention claimed is:

1. A device for providing an electrical therapy to a skin of a subject comprising:
   one or more electrode pads comprising a transmission surface, the one or more electrode pads comprising a first electrode and a second electrode;
   a power supply in electrical communication with the first and second electrodes; and
   a controller to regulate voltage, current, or both of an electrical signal supplied the first and second electrodes by the power supply,
   wherein the one or more electrode pads are shaped to conform to the skin of an eye, eyelid, eyelid margin, nose, or mouth of the subject,
   wherein the device is configured to generate a plurality of pulses, and
   wherein the device is configured to vaporize a biofilm.

2. The device of claim 1, wherein the controller supplies a first voltage to the first electrode, and a second voltage to the second electrode, thereby creating a voltage potential between the first electrode and the second electrode.

3. The device of claim 2, wherein the first and second electrode are configured to contact a skin surface to generate an electric current through the skin.

4. The device of claim 1, wherein the vaporizing a biofilm is via the electric current through the skin.

5. The device of claim 3, wherein the controller is configured to measure an impedance of the skin based on a measured impedance.

6. The device of claim 1, wherein the voltage of the electrical signal is about 0.1 V to about 20 V.

7. The device of claim 1, wherein the current of the electrical signal is less than about 5 milliamps (mA).

8. The device of claim 1, further comprising a housing and a wire lead, wherein the power supply and the controller are disposed within the housing, and wherein the wire lead connects the power supply and controller to the transmission surface.

9. The device of claim 1, wherein the current of the electrical signal is an alternating current signal.

10. The device of claim 1, wherein the current of the electrical signal is a direct current signal.

11. The device of claim 1, wherein the electrical therapy configured to treat acne, snoring, dry eye, premature aging, or a combination thereof.

* * * * *